United States Patent
Kim et al.

(10) Patent No.: US 10,332,136 B2
(45) Date of Patent: Jun. 25, 2019

(54) SMART WATCH, CONTROL METHOD THEREOF, NON-TRANSITORY COMPUTER READABLE STORAGE MEDIUM HAVING COMPUTER PROGRAM RECORDED THEREON AND SYSTEM FOR PROVIDING CONVENIENCE TO CUSTOMER

(71) Applicant: SK Planet Co., Ltd., Seongnam-si, Gyeonggi-do (KR)

(72) Inventors: Hyoung Seok Kim, Yongin-si (KR); Hwan Won Choi, Seoul (KR)

(73) Assignee: SK PLANET CO., LTD., Seongnam-si (KR)

( * ) Notice: Subject to any disclaimer, the term of this patent is extended or adjusted under 35 U.S.C. 154(b) by 524 days.

(21) Appl. No.: 14/835,359

(22) Filed: Aug. 25, 2015

(65) Prior Publication Data
US 2016/0063525 A1 Mar. 3, 2016

(30) Foreign Application Priority Data

Aug. 26, 2014 (KR) ........................ 10-2014-0111417

(51) Int. Cl.
*G06Q 30/02* (2012.01)
*G04G 21/02* (2010.01)
*A61B 5/00* (2006.01)
*A61B 5/11* (2006.01)

(52) U.S. Cl.
CPC ............ *G06Q 30/0203* (2013.01); *A61B 5/11* (2013.01); *A61B 5/681* (2013.01); *G04G 21/025* (2013.01)

(58) Field of Classification Search
CPC ...................................................... G06Q 30/02
See application file for complete search history.

(56) References Cited

U.S. PATENT DOCUMENTS

| | | | |
|---|---|---|---|
| 2001/0049470 A1* | 12/2001 | Mault | A61B 5/6824 600/300 |
| 2014/0063055 A1* | 3/2014 | Osterhout | G06F 3/005 345/633 |
| 2014/0349257 A1* | 11/2014 | Connor | G09B 19/0092 434/127 |

(Continued)

FOREIGN PATENT DOCUMENTS

| | | |
|---|---|---|
| CN | 102523493 A | 6/2012 |
| CN | 102933136 A | 2/2013 |

(Continued)

OTHER PUBLICATIONS

Office Action dated Nov. 27, 2018 for Chinese Application No. 201510515905.7, 7 pages.

*Primary Examiner* — Kurtis Gills
(74) *Attorney, Agent, or Firm* — Brinks Gilson & Lione

(57) ABSTRACT

The present invention provides, a smart watch, a method of controlling the smart watch, a non-transitory computer readable storage medium having a computer program recorded thereon, and a system for providing convenience to a customer. That is, the present invention can provide a smart watch that can provide product preference of a user on the basis of the user's behavior patterns and bodily changes and to provide a smart watch that can appropriately provide relevant information on the basis of user's product preference, so it can improve convenience in use.

8 Claims, 8 Drawing Sheets

(56) References Cited

U.S. PATENT DOCUMENTS

2015/0253885 A1\* 9/2015 Kagan .................. G06F 3/0482
368/10
2015/0356497 A1\* 12/2015 Reeder .................... H04Q 9/00
705/28
2015/0379601 A1\* 12/2015 Ouimet ............. G06Q 30/0613
705/26.41

FOREIGN PATENT DOCUMENTS

| CN | 103339649 A | 10/2013 |
| CN | 103919537 A | 7/2014 |
| WO | WO 2012/158234 A2 | 11/2012 |

\* cited by examiner

SMART WATCH, CONTROL METHOD THEREOF, NON-TRANSITORY COMPUTER READABLE STORAGE MEDIUM HAVING COMPUTER PROGRAM RECORDED THEREON AND SYSTEM FOR PROVIDING CONVENIENCE TO CUSTOMER

CROSS-REFERENCE TO RELATED APPLICATION

This application claims the benefit of Korean Application No. 10-2014-0111417 filed on Aug. 26, 2014 with the Korean Intellectual Property Office, the disclosure of which is incorporated herein by reference.

BACKGROUND OF THE INVENTION

1. Field of the Invention

The present invention relates to a smart watch, a control method thereof, a non-transitory computer readable storage medium having computer program recorded thereon, and a system for providing convenience to customer, and particularly, to seller glasses product preference of a user, control method thereof, a non-transitory computer readable storage medium having computer program recorded thereon, and a system for providing convenience to customer.

2. Description of the Related Art

Entering 2000's, the market of terminals increasingly requiring mobility and capable of connecting with the internet such as a smart phone has greatly grown with correspondence of technical development and an increase in demand by users.

In tandem of the marketability, smart phones are increasingly popularized, and an increase in size of smart phones has increased a demand for another terminal making it possible to check contents on a smart phone even without taking the smart phone out of a pocket or a bag.

A smart watch has been actively studied and developed as a wearable terminal that can satisfy the demand in the market.

A smart watch can be put on a wrist, similar to common watches, and can display contents in cooperation with or independently from a smart phone, in addition to showing time.

Meanwhile, it has been recently attempt to apply a smart watch to various industries with technical development. Accordingly, study and development for applying wearable display devices to various industries and services have been required.

PRIOR ART DOCUMENT

Patent Document

Korean patent Publication No. 10-2013-0125123 [Title: Method and system for providing online coupon service interworking social network service]

SUMMARY OF THE INVENTION

An object of the present invention is to provide a smart watch that can provide product preference of a user on the basis of the user's behavior patterns and bodily changes, a method of controlling the smart watch, a non-transitory computer readable storage medium having a computer program recorded thereon, and a system for providing convenience to a customer.

Another object of the present invention is to provide a smart watch that can appropriately provide relevant information on the basis of user's product preference, a method of controlling the smart watch, a non-transitory computer readable storage medium having a computer program recorded thereon, and a system for providing convenience to a customer.

According to an aspect of the present invention, a smart watch may include: a product information sensing unit that senses product information; a heartbeat sensor that acquires heartbeat data; a preference information acquiring unit that acquires user's preference information on the basis of the heartbeat data about the product information; and a display unit that displays the user's preference information.

As an example of the present invention, the smart watch may further include a control unit that provides marketing information about relevant products, when the user's preference information exceeds a predetermined level.

As an example of the present invention, the marketing information may include at least one of product advertisement data, product specification data, and relevant product data.

As an example of the present invention, the product information sensing unit may include a sensing module that senses products or product information on tags in a store.

According to another aspect of the present invention, a method of controlling a smart watch may include: sensing product information through a product information sensing unit; acquiring heartbeat data through a heartbeat sensor; acquiring user's preference information on the basis of heartbeat data about the product information through the preference information acquiring unit; and displaying the user's preference information through a display unit.

As an example of the present invention, the sensing of product information may acquire user's motions sensed by a motion sensing unit and may sense product information on the basis of the user's motions.

As an example of the present invention, the acquiring of user's preference information may acquire user's preference information on the basis of a heartbeat rate sensed for a predetermined period.

As an example of the present invention, the acquiring of user's preference information may acquire user's motions sensed by a motion sensing unit and may acquire user's preference information on the basis of the user's motions.

As an example of the present invention, the acquiring of user's preference information may acquire user's preference information on the basis of information about how long a user checks a product.

According to another aspect of the present invention, a computer program comprising a set of instructions, when executed, arranged to perform the method of controlling a smart watch may be kept in a non-transitory computer readable storage medium having a computer program recorded thereon.

According to another aspect of the present invention, a system for providing convenience to a customer may include: a smart watch that senses product information, acquires heartbeat data and user's motions, and transmits the product information, the heartbeat data, and the user's motions; and a service providing device that acquires user's preference information on the basis of the product information, the heartbeat data, and the user's motions, acquires marketing information on the basis of the user's preference information, and transmits the marketing information to the smart watch.

According to the present invention, it is possible to provide a smart watch that can provide product preference of a user on the basis of the user's behavior patterns and bodily changes, a method of controlling the smart watch, a non-transitory computer readable storage medium having a computer program recorded thereon, and a system for providing convenience to a customer.

Further, according to the present invention, it is possible to provide a smart watch that can appropriately provide relevant information on the basis of user's product preference, a method of controlling the smart watch, a non-transitory computer readable storage medium having a computer program recorded thereon, and a system for providing convenience to a customer.

DETAILED DESCRIPTION OF THE PREFERRED EMBODIMENTS

Figure 1:
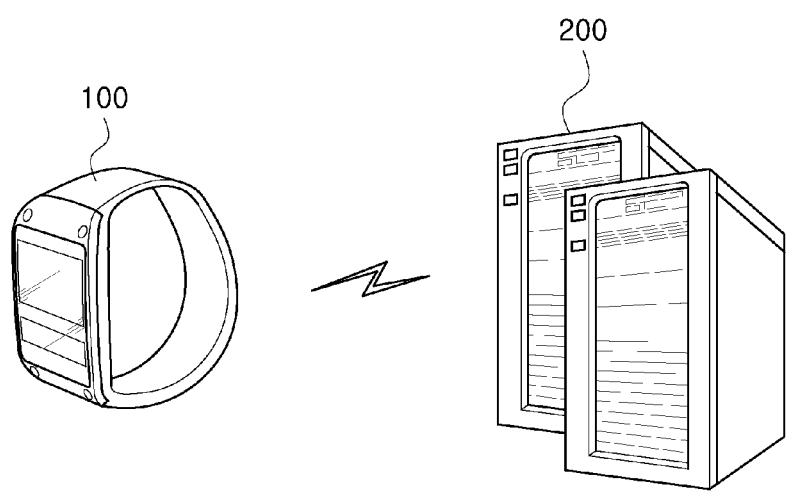
FIG. 1 is a diagram illustrating the configuration of a system for providing convenience to a customer according to an embodiment of the present invention.

It should be noted that technical terminologies used herein are used only in order to describe specific embodiments rather than limiting the present invention. Further, the technical terminologies used here should be construed as being generally understood by those skilled in the art unless defined as specific meanings, not construed as being excessively general meanings or excessively narrow meanings. Further, if the technical terminologies used herein are wrong technical terminologies that cannot exactly express the spirit of the present invention, they should be replaced by technical terminologies that can be correctly understood by those skilled in the art. Further, common terms used herein should be construed in accordance with dictionary definitions or contexts, not being as excessively narrow meanings.

The singular forms used herein are intended to include the plural forms as well, unless the context clearly indicates otherwise. Terms "composed of" or "include" used herein should not construed as necessarily including all of various components or various steps, but construed that they may not include some of the components or steps or may further include additional components or steps.

Further, terms including ordinal numbers such as 'first' and 'second' may be used to describe various components, but the components are not to be construed as being limited to the terms. The terms are used to distinguish one component from another component. For example, the 'first' component may be named the 'second' component, and vice versa, without departing from the scope of the present invention.

Hereinafter, embodiments of the present invention will be described in detail with reference to the accompanying drawings, like reference numerals are given to like or similar components regardless of the figure numbers, and repeated description is not provided.

Further, in describing the present invention, detailed descriptions of well-known technologies will be omitted so as not to obscure the description of the present invention with unnecessary detail. Further, it should be noted that the accompanying drawings are provided only for easier understanding of the spirit of the present invention and should not be construed as limiting the spirit of the present invention.

A smart watch described herein may mean a watch type electronic device that a person can wear. Further, the smart watch is a small electronic device including a central processing device, a communication unit, a memory, and a display unit, and the like, and capable of processing various data related to services.

Further, the service providing device described herein is a general term including all kinds of electronic devices keeping data relating to services required by a smart watch, transmitting/receiving data to/from user equipment, and supporting operation of applications in the user equipment by transmitting/receiving data to/from the smart watch.

Further, an object described herein is an object to which user's intention or motion is applied, and for example, may be an image, a moving image, an icon, sound, and a data file. Further, other various types of objects may be considered.

FIG. 1 is a diagram illustrating the configuration of a system for providing convenience to a customer according to an embodiment of the present invention.

As illustrated in FIG. 1, a system for providing convenience to a customer may include a smart watch 100 and a service providing device 200. The components of the system for providing convenience to a customer illustrated in FIG. 1 are not all necessary components, and the system for providing convenience to a customer may be composed of components much or less than the components illustrated in FIG. 1.

According to the present invention, the smart watch 100 can acquire heartbeat data every time a customer checks a plurality of products. Further, the smart watch 100 can transmit a plurality of products information and heartbeat data to the service providing device 200.

The service providing device 200 can acquire information about user's preference on the basis of a plurality of products information and heartbeat data and acquire marketing information on the basis of user's preference information. Further, the service providing device 200 can transmit the acquired marketing information to the smart watch 100.

A user can check his/her product preference through the smart watch 100 and receive various items of information about preferred products.

Thereon, according to an embodiment of the present invention, a user of the smart watch can check his/her product preference and receive various items of information about preferred product and a product seller can use the user's product preference for marketing.

Figure 2:
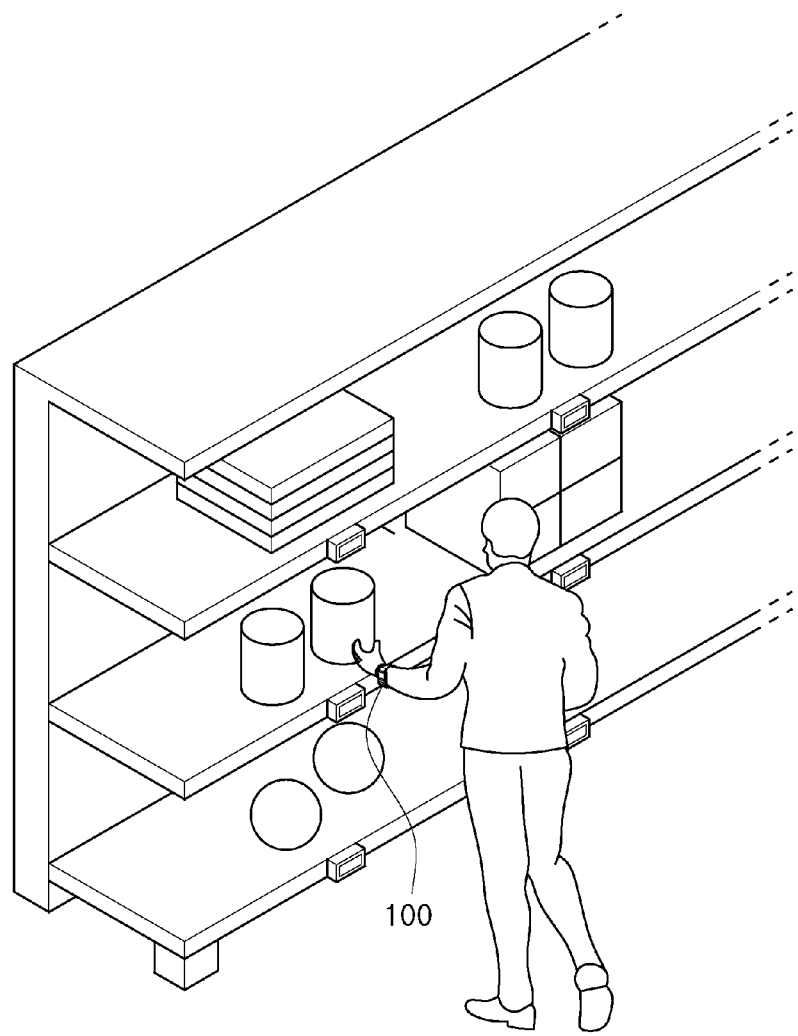
FIG. 2 is a diagram illustrating in detail use of the smart watch according to an embodiment of the present invention.

FIG. 2 is a diagram illustrating in detail use of the smart watch according to an embodiment of the present invention.

As illustrated in FIG. 2, a customer can check products in a store, wearing the smart watch 100. In this case, the smart watch 100 can sense products that the customer checks, by recognizing a tag on the product, sensing the user's motion, and the like.

Further, the smart watch 100 can sense heartbeat data and motions of the user while the user checks products. In this case, the smart watch 100 can acquire user's preference information based on heartbeat data of the user and the user's motions and display them.

In this case, the smart watch can help the user do the shopping by displaying product advertisement data, product specification data, and relevant product data, in addition to the user's preference information.

Figure 3:
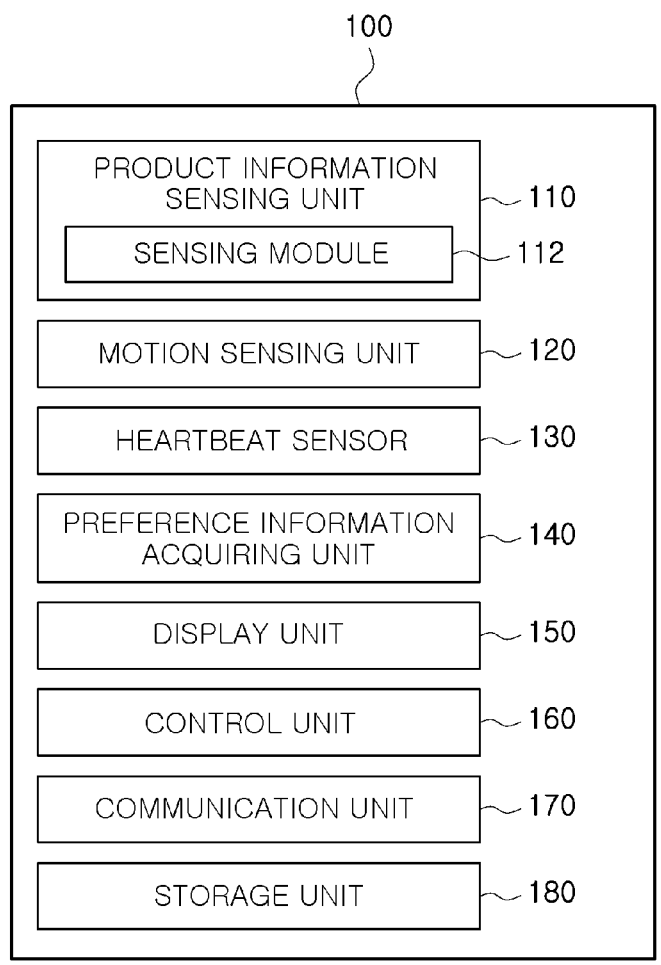
FIG. 3 is a block diagram illustrating a smart watch according to an embodiment of the present invention.

FIG. 3 is a block diagram illustrating the smart watch 100 according to an embodiment of the present invention.

As illustrated in FIG. 3, the smart watch 100 may include a product information sensing unit 110, a motion sensing unit 120, a heartbeat sensor 130, a preference information acquiring unit 140, a display unit 150, a control unit 160, and a communication unit 170, and a storage unit 180. The components of the smart watch 100 illustrated in FIG. 3 are not all necessary components, and the smart watch 100 may be composed of components much or less than the components illustrated in FIG. 3.

The product information sensing unit 110 can sense products that a user checks in a store.

Figure 4A:
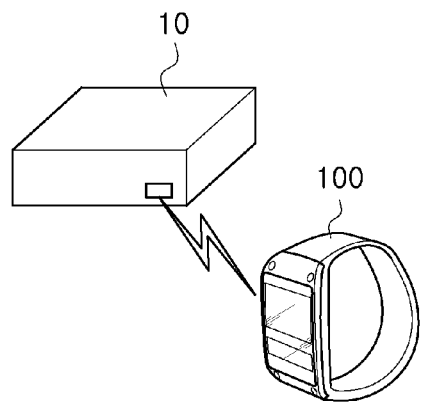
FIGS. 4A and 4B are diagrams illustrating a way that a smart watch recognizes product information.
Figure 4B:
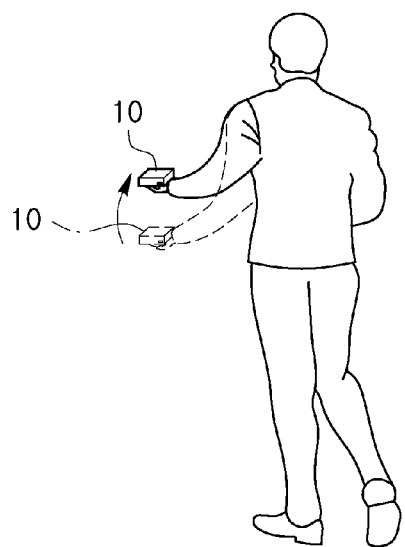

FIGS. 4A and 4B are diagrams illustrating a way that a smart watch recognizes product information.

FIG. 4A is a diagram illustrating a way that a smart watch recognizes product information, using a sensing module.

The product information sensing unit 110 can include a sensing module 112 that senses products or product information on tags in a store. For example, the sensing module 112 may have a function of recognizing barcodes or a function of NFC (Near Field Communication).

Referring to FIG. 4A, the smart watch 100 can sense a product 10 on the basis of product information on the product 10.

FIG. 4B is a diagram illustrating a way that a smart watch recognizes product information, using a motion sensing unit.

The smart watch 100 can includes the motion sensing unit 120 that senses user's motions. For example, the motion sensing unit 120 may include a gyro sensor or an angular speed sensor, so it can sense motions of a user wearing the smart watch 100.

Referring to FIG. 4B, when a user makes a specific action of pick the product 10 up, the smart watch 100 can acquire information about the product that the user holds, using local communication.

That is, the product information sensing unit 110 can acquire the user's motion sensed by the motion sensing unit 120 and sense product information on the basis of the user's motion.

The heartbeat sensor 130 can acquire heartbeat data of the user wearing the smart watch 100. For example, the heartbeat data may include a heartbeat rate and intensity of heartbeat.

Figure 5A:
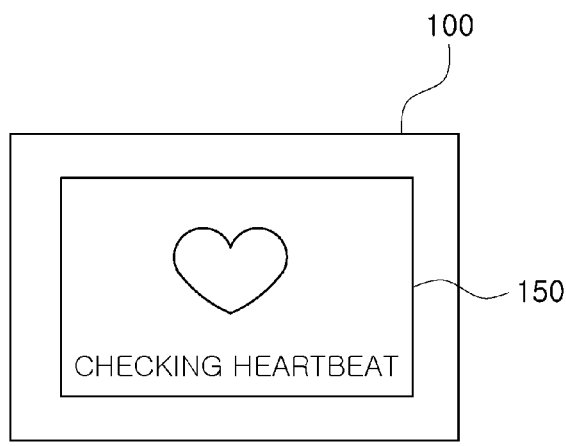
FIGS. 5A and 5B are diagrams illustrating data displayed on a smart watch when a user checks a specific article.
Figure 5B:
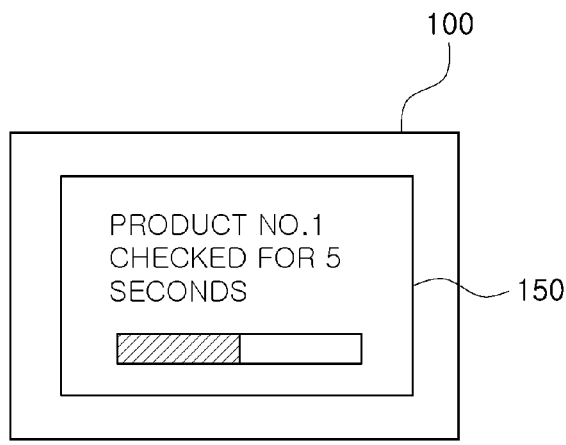

FIGS. 5A and 5B are diagrams illustrating data displayed on a smart watch when a user checks a specific article.

FIG. 5A is a diagram illustrating a process of acquiring heartbeat data by means of a smart watch.

When a user wearing a smart watch checks a specific article in a store, the smart watch can acquire heartbeat data of the user and display an object showing this situation on the display unit 150.

FIG. 5B is a diagram illustrating a process of sensing a user's motion by means of a smart watch.

When a user wearing a smart watch checks a specific article in a store, the smart watch can sense motions of the user.

In this case, the motion sensing unit 120 can sense information about how long the user is checking a specific article (information about time for which the user checks a product).

The preference information acquiring unit 140 can acquire user's preference information on the basis of the heartbeat data acquired by the heartbeat sensor 130.

In detail, the preference information acquiring unit 140 can acquire heartbeat data of the user checking a specific product and can acquire heartbeat data every time the user checks a plurality of products. Further, the preference information acquiring unit 140 can acquire user's preference information on the basis of the heartbeat rate sensed for a predetermined period.

Meanwhile, the information about the heartbeat rate of the user for preferred products can be kept in the storage unit 180. Accordingly, the preference information acquiring unit 140 can acquire user's preference information on the basis of the sensed heartbeat rate and the data kept in the storage unit 180.

Further, the preference information acquiring unit 140 can acquire user's preference information on the basis of the user's motions acquired by the motion sensing unit 120.

For example, the preference information acquiring unit 140 can acquire user's motions sensed by the motion sensing unit 120 and can acquire user's preference information on the basis of the user's motions. In detail, the preference information acquiring unit 140 can acquire user's preference information on the basis of information about how long the user checks a product. For example, when a user checks a product for a long time, the user's preference can be estimated to be high.

The display unit 150 can display the user's preference information acquired by the preference information acquiring unit 140.

Figure 6A:
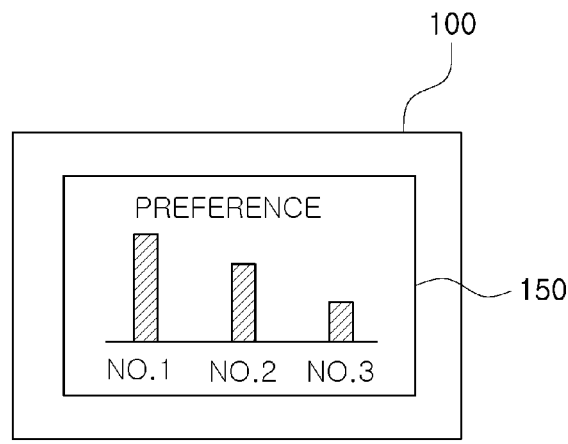
FIGS. 6A and 6B are diagrams illustrating information about user's preference displayed on a display unit of a smart watch.
Figure 6B:
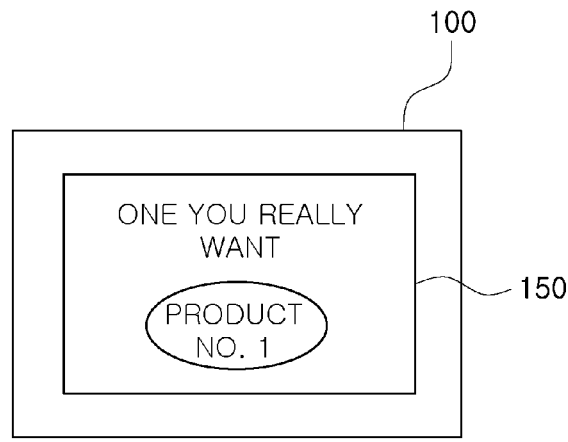

FIGS. 6A and 6B are diagrams illustrating information about user's preference displayed on a display unit of a smart watch.

As illustrated in FIG. 6A, the display unit 150 can display user's preference information about a plurality of products.

Further, as illustrated in FIG. 6B, the display unit 150 can display the information about the most preferred product of a plurality of products.

Meanwhile, the control unit 160 can provide marketing information based on the user's preference. For example, the control unit 160 can provide marketing information about relevant products, when the user's preference information about a specific product exceeds a predetermined level. The marketing information may include at least one of product advertisement data, product specification data, and relevant product data.

The marketing information can be kept in the storage 180 or can be provided from the service providing device 200.

The communication unit 170 can transmit/receive data to/from the service providing device 200. For example, the communication unit 170 can transmit product information, heartbeat data, and user's motions to the service providing device 200. Further, the communication unit 170 can receive the user's preference information and the marketing information acquired by the service providing device 200 on the basis of the product information, heartbeat data, and user's motions.

That is, although it was described above that the functions of the preference information acquiring unit 140, the control unit 160, and the storage unit 180 were given to the smart watch 100 for the convenience of description, the functions of the preference information acquiring unit 140, the control unit 160, and the storage unit 180 may be given to at least one of the smart watch 100 and the service providing device 200.

Figure 7A:
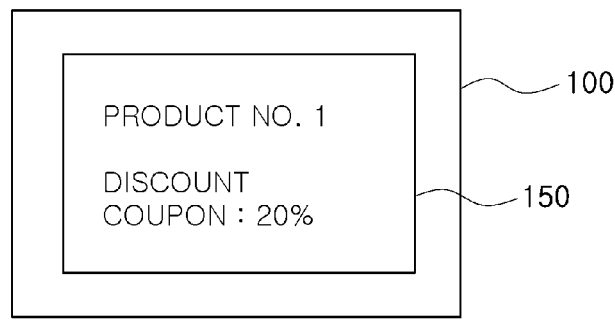
FIGS. 7A to 7C are diagrams illustrating marketing information displayed on a display unit of a smart watch.
Figure 7B:
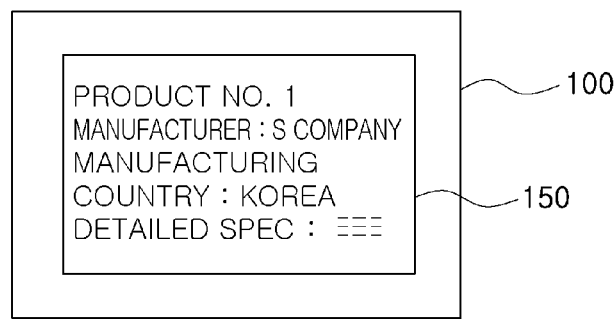
Figure 7C:
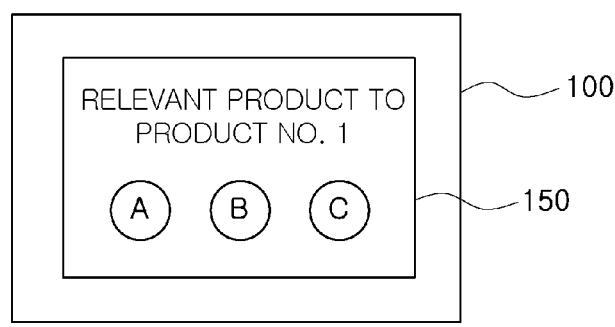

FIGS. 7A to 7C are diagrams illustrating marketing information displayed on a display unit of a smart watch.

As illustrated in FIG. 7A, marketing information may be product advertisement data for a product that a user prefers much.

Further, as illustrated in FIG. 7B, marketing information may be product specification data for a product that a user prefers much.

Alternatively, as illustrated in FIG. 7C, marketing information may be product data relevant to a product that a user prefers much.

Figure 8:
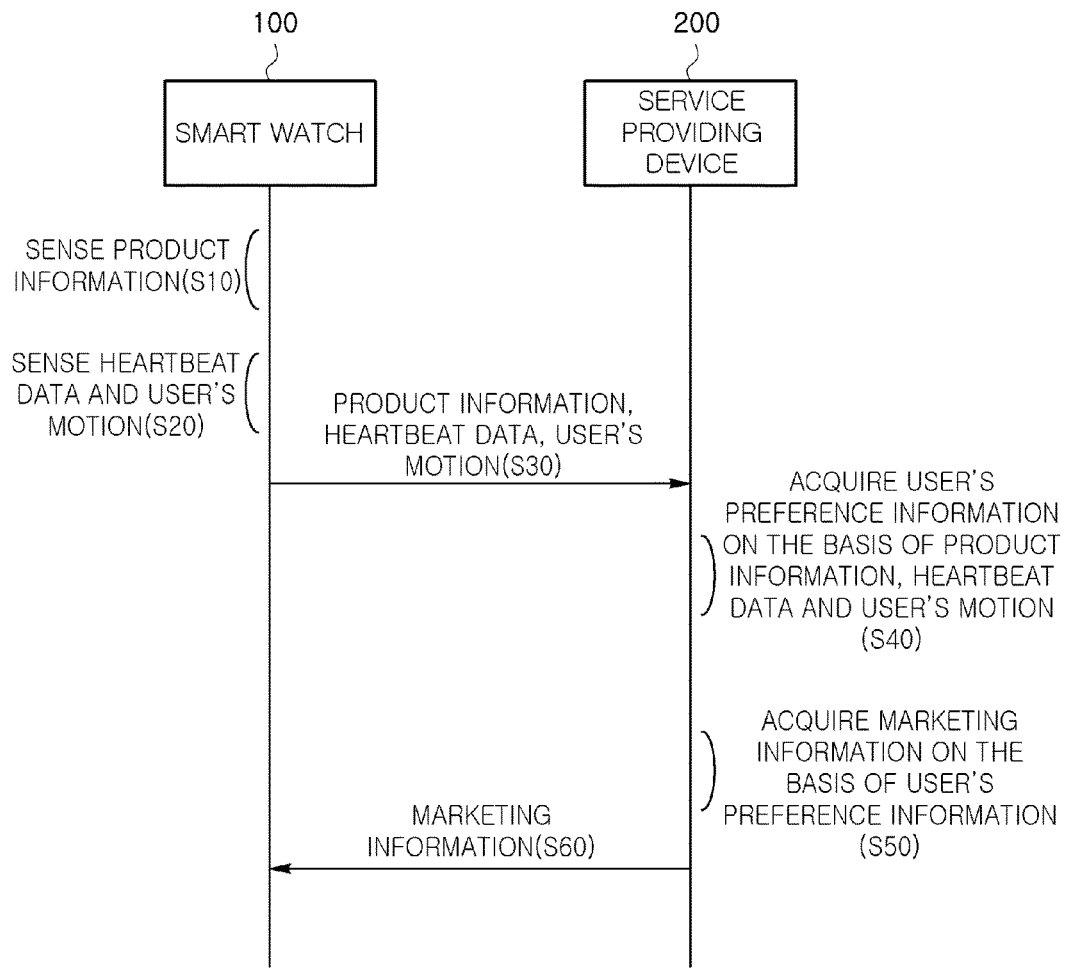
FIG. 8 is a diagram illustrating a method of controlling a system for providing convenience to a customer according to an embodiment of the present invention.

FIG. 8 is a diagram illustrating a method of controlling a system for providing convenience to a customer according to an embodiment of the present invention.

As illustrated in FIG. 8, the smart watch 100 can sense product information (S10). Further, the smart watch can sense heartbeat data about the sensed product information, and user's motions (S20). In this case, the smart watch can sense product information of a plurality of products, heartbeat data, and user's motions.

Thereafter, the smart watch 100 can transmit the sensed product information, heartbeat data, and user's motions to the service providing device 200 (S30).

The service providing device 200 receiving the product information, heartbeat data, and user's motions from the smart watch 100 can acquire user's preference information on the basis of at least one of the received product information, heartbeat data, and user's motions (S40).

Thereafter, the service providing device 200 can acquire marketing information on the basis of the acquired user's preference information (S50).

Further, the service providing device 200 can transmit the acquired marketing information to the smart watch 100.

The smart watch 100 receiving the marketing information can display the received marketing information.

According to this configuration, a user can be helped to purchase products by checking preference of the products through the smart watch.

Further, a user can appropriately receive relevant information on the basis of the product preference.

Further, a seller can perform accurate target marketing on the basis of the preference of customers.

A method of controlling a smart watch according to an embodiment of the present invention can be recorded in a computer program, and codes and code segments of the computer program can be easily inferred by computer programmers in the field. The computer program is stored in non-transitory computer readable storage media, and read and executed by user equipment according to an embodiment of the present invention, so the method of controlling the user equipment can be implemented.

The non-transitory computer readable storage media include a magnetic recording storage medium, an optical recording storage medium, and a carrier wave storage medium. A computer program for achieving the method of controlling a smart watch according to an embodiment of the present invention may be stored and installed in a built-in memory in the smart watch, and the like. Alternatively, an external memory such as a smart card in which a computer program for achieving the method of controlling a smart watch according to an embodiment of the present invention is stored and installed may be mounted on the smart watch through an interface.

It should be understood that the present invention may be changed and modified by those skilled in the art without departing from the scope of the present invention. Accordingly, the embodiment described herein are provided not to limit, but to explain the spirit of the present invention and the spirit and the scope of the present invention are not limited by the embodiments. The protective range of the present disclosure should be construed on the basis of claims and all the technical spirits in the equivalent range should be construed as being included in the scope of the right of the present disclosure.

According to the present invention, it is possible to provide a smart watch that can provide product preference of a user on the basis of the user's behavior patterns and bodily changes and to provide a smart watch that can appropriately provide relevant information on the basis of user's product preference, so it can be used in various fields such as the fields of commercial transaction and marketing by improving convenience in use.

What is claimed is:

1. A smart watch comprising:
    a motion sensor configured to:
        sense a motion of a user including picking up a product; and
        sense information regarding duration of holding the product by the user;
    a product sensor configured to sense the product using local communication when the motion sensor senses that the user holds the product;
    a heartbeat sensor configured to acquire heartbeat data of the user;
    a preference information collector configured to:
        measure a first heartbeat of the user for a predetermined amount of time when the user holds a first product;
        measure a second heartbeat of the user for the predetermined amount of time when the user holds a second product;
        compare the first heartbeat of the user with the second heartbeat of the user;
        measure a first duration of holding the first product by the user;
        measure a second duration of holding the second product by the user;
        compare the first duration with the second duration; and
        determine that a preferred product of the user is the first product when the first heartbeat is greater than the second heartbeat, or the first duration is greater than the second duration; and
    a display screen configured to display the preference information of the user including the preferred product of the user.

2. The smart watch of claim 1, further comprising:
    a controller configured to provide product information corresponding to the product when the preference information of the user exceeds a predetermined level.

3. The smart watch of claim 2, wherein the product information comprises at least one of product advertisement data, product specification data, or relevant product data.

4. The smart watch of claim 1, wherein the product sensor further comprises:
    a sensing module configured to sense the product or product information included on tags in a store.

5. A method of controlling a smart watch, the method comprising:

sensing, with a motion sensor, a motion of a user including picking up a product;
sensing, with the motion sensor, information regarding duration of holding the product by the user;
when it is sensed that the user holds the product, sensing, with a product sensor, the product using local communication;
acquiring, with a heartbeat sensor, heartbeat data of the user;
when the user holds a first product, measuring, with a preference information collector, a first heartbeat of the user for a predetermined amount of time;
when the user holds a second product, measuring, with the preference information collector, a second heartbeat of the user for the predetermined amount of time;
comparing, with the preference information collector, the first heartbeat of the user with the second heartbeat of the user;
measuring, with the preference information collector, a first duration of holding the first product by the user;
measuring, with the preference information collector, a second duration of holding the second product by the user;
comparing, with the preference information collector, the first duration with the second duration;
determining, with the preference information collector, that a preferred product of the user is the first product when the first heartbeat is greater than the second heartbeat, or the first duration is greater than the second duration; and
displaying, with a display screen, the preference information of the user including the preferred product of the user.

6. The method of claim 5, wherein acquiring the preference information of the user further comprises:
acquiring the preference information of the user based on a rate of the heartbeat of the user sensed for a predetermined amount of period.

7. The method of claim 5, wherein acquiring the preference information of the user further comprises:
acquiring, with the motion sensor, the motion of the user; and
acquiring the preference information of the user based on the motion of the user.

8. A system for providing convenience to a customer, the system comprising:
a smart watch configured to:
sense a product held by a user;
acquire heartbeat data of the user and a motion of the user;
measure a first heartbeat of the user for a predetermined amount of time when the user holds a first product;
measure a second heartbeat of the user for the predetermined amount of time when the user holds a second product;
measure a first duration of holding the first product by the user;
measure a second duration of holding the second product by the user; and
transmit, to a service providing device, the heartbeat data of the user including the first heartbeat of the user and the second heartbeat of the user, and the motion of the user including the first duration and the second duration; and
the service providing device configured to:
compare the first heartbeat of the user with the second heartbeat of the user;
compare the first duration with the second duration;
determine that a preferred product of the user is the first product when the first heartbeat is greater than the second heartbeat, or the first duration is greater than the second duration;
acquire information regarding the first product based on determination that the preferred product of the user is the first product; and
transmit the information regarding the first product to the smart watch.

* * * * *